(12) United States Patent
Cheradame et al.

(10) Patent No.: US 8,658,150 B2
(45) Date of Patent: Feb. 25, 2014

(54) POLYMER DERIVED FROM LINEAR POLYETHYLENIMINE FOR GENE TRANSFER

(75) Inventors: Hervé Cheradame, Neuilly sur Seine (FR); Mathieu Sassatelli, Ballancourt sur Essonne (FR); Philippe Guegan, Paris (FR); Patrick Midoux, Saint Denis de l'Hotel (FR); Chantal Pichon, Saint Denis de l'Hotel (FR)

(73) Assignees: Centre National de la Recherche Scientifique, Paris (FR); Universite d'Orleans, Orleans (FR); Universite d'Evry val d'Essonne, Evry (FR)

( * ) Notice: Subject to any disclaimer, the term of this patent is extended or adjusted under 35 U.S.C. 154(b) by 395 days.

(21) Appl. No.: 12/920,971

(22) PCT Filed: Mar. 4, 2009

(86) PCT No.: PCT/EP2009/052530
§ 371 (c)(1),
(2), (4) Date: Dec. 28, 2010

(87) PCT Pub. No.: WO2009/112402
PCT Pub. Date: Sep. 17, 2009

(65) Prior Publication Data
US 2011/0091407 A1    Apr. 21, 2011

(30) Foreign Application Priority Data
Mar. 5, 2008 (FR) .................................. 08 51434

(51) Int. Cl.
*A61K 31/00* (2006.01)
(52) U.S. Cl.
USPC ............................................. 424/78.3
(58) Field of Classification Search
USPC ............................................. 424/78.3
See application file for complete search history.

(56) References Cited

U.S. PATENT DOCUMENTS

| | | | |
|---|---|---|---|
| 5,595,897 A | 1/1997 | Midoux et al. | |
| 5,677,384 A | 10/1997 | Detering et al. | |
| 5,681,543 A | 10/1997 | Schmitt-Willich et al. | |
| 6,013,240 A | 1/2000 | Behr et al. | |
| 6,200,956 B1 | 3/2001 | Scherman et al. | |
| 6,372,499 B1 | 4/2002 | Midoux et al. | |
| 6,586,524 B2 | 7/2003 | Sagara | |
| 7,141,077 B2 | 11/2006 | Detering et al. | |
| 7,163,695 B2 | 1/2007 | Mixson | |
| 7,238,451 B2 | 7/2007 | Frech et al. | |
| 2003/0027784 A1 | 2/2003 | Kissel et al. | |
| 2003/0147958 A1 | 8/2003 | Ahn et al. | |
| 2004/0048819 A1 | 3/2004 | Simon et al. | |
| 2005/0101552 A1 | 5/2005 | Demeneix et al. | |
| 2006/0093674 A1 | 5/2006 | Slobodkin et al. | |
| 2006/0210635 A1 | 9/2006 | Laurent et al. | |
| 2010/0129371 A1 | 5/2010 | Scherman et al. | |

FOREIGN PATENT DOCUMENTS

| | | |
|---|---|---|
| EP | 0 330 193 B1 | 9/1992 |
| EP | 0 703 972 B1 | 1/1997 |
| EP | 0 987 029 A1 | 3/2000 |
| EP | 0 753 070 B1 | 9/2002 |
| EP | 1 135 481 B1 | 2/2004 |
| EP | 0 946 744 B1 | 8/2004 |
| EP | 1 044 008 B1 | 1/2006 |
| EP | 1 844 772 A1 | 10/2007 |
| FR | 2 814 370 | 3/2002 |
| FR | 2 849 602 | 7/2004 |
| WO | WO 96/02655 A1 | 2/1996 |
| WO | WO 96/25508 | 8/1996 |
| WO | WO 97/12061 | 4/1997 |
| WO | WO 00/03694 | 1/2000 |

(Continued)

OTHER PUBLICATIONS

Overberger et al., J. Polymer Sci., vol. 15, 1863-1868 (1977).*

(Continued)

*Primary Examiner* — Michael G Hartley
*Assistant Examiner* — Robert Cabral
(74) *Attorney, Agent, or Firm* — Foley & Lardner LLP (57) ABSTRACT

The invention relates to a static copolymer of linear polyethylenimine that comprises two monomer units of the following formulas I and II, in which $R_1$ is a hydrogen atom or a $C_1$-$C_6$ alkyl radical, $R_2$ is a hydrogen atom, a $C_1$-$C_6$ alkyl, aryl or aralkyl group, wherein the alkyl group is a $C_1$-$C_6$ one, n is a number between 1 and 99% of the total monomers, m is a number between 1 and 99% of the total monomers, and advantageously m+n=100%. The invention also relates to complexes of this copolymer with a nucleic acid, and to the use thereof in in vivo, in vitro or ex vivo gene transfection.

18 Claims, 5 Drawing Sheets

(56) References Cited

FOREIGN PATENT DOCUMENTS

| WO | WO 01/03667 A1 | 1/2001 |
|---|---|---|
| WO | WO 01/47496 A1 | 7/2001 |
| WO | WO 03/008555 A2 | 1/2003 |
| WO | WO 2004/026941 A1 | 4/2004 |
| WO | WO 2004/033620 A2 | 4/2004 |
| WO | WO 2004/099288 A1 | 11/2004 |
| WO | WO 2007/012671 A2 | 2/2007 |

OTHER PUBLICATIONS

Jeong et al., J. Controlled Release 73 (2001) 391-399.*
Carrabino et al., J. Gene Med. 2005; 7: 1555-1564.*
Hanneke et al., Macromolecules, 2010, 43, 927-933 (Published on Web Dec. 22, 2009).*
Arote et al., "A biodegradable poly(ester amine) based on polycaprolactone and polyethylenimine as a gene carrier," Biomaterials, pp. 735-744, vol. 28, 2007.
Bentolila et al., "Poly(N-acryl amino acids): A New Class of Biologically Active Polyanions," J. Med. Chem., pp. 2591-2600, vol. 43, No. 13, 2000.
Boussif et al., "A versatile vector for gene and Oligonucleotide transfer into cells in culture and in vivo: Polyethylenimine," Proc. Natl. Acad. Sci. USA, pp. 7297-7301, vol. 92, 1995.
Brissault et al., "Synthesis of linear polyethylenimine derivatives for DNA transfection," Bioconjug. Chem. 2003, Abstract, [online] <URL: http://www.ncbi.nlm.nih.gov/sites/entrez?Db=pubmed&Cmd=ShowDetailView&Ter . . . >, Dec. 26, 2007.
Brissault et al., "Linear topology confers in vivo gene transfer activity to polyethylenimines," Bioconjug. Chem., 2006, Abstract, [online] [Retrieved Dec. 26, 2007] <URL: http://www.ncbi.nlm.nih.gov/sites/entrez?Db=pubmed&Cmd=ShowDetailView&Ter . . . >.
Eliyahu et al., "Polymers for DNA Delivery," Molecules, pp. 34-64, vol. 10, 2005.
Forrest et al., "A Degradable Polyethylenimine Derivative with Low Toxicity for Highly Efficient Gene Delivery," Bioconjugate Chem., pp. 934-940, vol. 14, No. 5, 2003.
Kim et al., "A Degradable Hyperbranched Poly(ester amine) Based on Poloxamer Diacrylate and Polyethylenimine as a Gene Carrier," Macromol. Biosci., pp. 611-619, vol. 7, 2007.
Mockey et al., "mRNA-based cancer vaccine: prevention of B16 melanoma progression and metastasis by systemic injection of MART1 mRNA histidylated lipopolyplexes," Cancer Gene Ther., 2007, Abstract, [online] [Retrieved Dec. 26, 2007] <URL: http://www.ncbi.nlm.nih.gov/sites/entrez?Db=pubmed&Cmd=ShowDetailView&Ter . . . >.
Nimesh et al., "Influence of acyl chain length on transfection mediated by acylated PEI nanoparticles," Int. J. Pharm., 2007, Abstract, [online] [Retrieved Dec. 26, 2007] <URL: http://www.ncbi.nlm.nih.gov/sites/entrez?Db=PubMed&Cmd=ShowDetailView&Ter . . . >.
Park et al., "Degradable polyethylenimine-alt-poly(ethylene glycol) copolymers as novel gene carriers," J. Controlled Release, pp. 367-380, vol. 105, 2005.
Pichon et al., "Zinc improves gene transfer mediated by DNA/cationic polymer complexes," J. Gene Med., pp. 548-559, vol. 4, 2002.
International Search Report, issued in application No. PCT/EP2009/052530 on May 7, 2009.
Swami et al., "Imidazolyl-PEI modified nanoparticles for enhanced gene delivery," Int'l. J. Pharma., pp. 180-192, vol. 335, 2007.

\* cited by examiner

POLYMER DERIVED FROM LINEAR POLYETHYLENIMINE FOR GENE TRANSFER

The invention relates to polyethylenimines and their uses in gene transfer with view to therapeutic applications.

In these applications, it is sought to correct genetic defects in target cells. The gene transfer may be carried out in vitro, ex vivo or in vivo. In operations carried out in vitro and ex vivo, it is sought to change the biological operation of cells within a culture, while in vitro administration on an animal or a patient intends to directly act on target tissues or organs, in order to modify protein biosyntheses. The main problem against which the gene transfer technique comes up, lies in the efficiency of the transfer into the targeted tissues or cells, with a high level of expression of the desired gene. The gene transfer is carried out by means of complexes essentially consisting of two portions. On the one hand, the active element is a nucleic acid, a plasmid, a DNA or RNA fragment. On the other hand, a protection, which may also include functions capable of assisting with the localization of the complex on the desired target cells or tissues, may also be present. This protection is generally designated as gene transfer vector, for which two main types are distinguished, viral vectors and synthetic (or non-viral) vectors. It is in this last category that the present invention is located.

Non-viral vectors in turn are subdivided into two main classes, cationic lipids or polymeric vectors. Regardless of the vector, formulations are sought, which are always more effective with a toxicity as reduced as possible, so that they may be used as a basis for therapeutic treatment. Positive polyelectrolytes form a set of polymeric vectors particularly suitable for gene transfer, insofar that their positive charge gives them properties for complexation of DNA and plasmids, and for interaction with the targeted cell surfaces. The resulting complex has size and surface charge characteristics such that its internalization in certain cells is highly promoted. Among positive polyelectrolytes already used for gene transfer, mention has to be made of poly-L-lysine and its derivatives, of chitosan and its derivatives as well as saccharides functionalized by amine functions, of poly(dimethylaminoethyl methacrylate), polyethylenimine (PEI) and its derivatives. The invention relates to this last class of positive polyelectrolytes based on PEI.

Poly(ethylenimine)s (PEIs) were the first materials of the positive polyelectrolyte type to have been introduced into the field of synthetic cationic polymeric vectors by Boussif et al., in 1995 (Proc. Natl. Acad. Sci. USA, 1995, 92, 7297-7301). Two types of PEI are distinguished, depending on the macromolecular structure; PEI with a linear macrostructure (LPEI obtained by hydrolysis of poly(2-alkyl-2-oxazoline)) on the one hand, and PEI with a branched structure (BPEI, obtained by polymerization of ethylenimine) on the other hand. These polymers of relatively good efficiency have become a reference as regards gene transfer by means of non-viral vectors, although this efficiency is still insufficient for allowing development of hereditary disease therapeutic treatment (Eliyahu et al., Molecules 2005, 10, 34-64). These polymers further have some toxicity, generally ascribed to their strong positive charge density on the macromolecular backbone. These vectors have been the subject of many modification proposals with the purpose of either improving transfection efficiency, or reducing toxicity. Thus, U.S. Pat. No. 6,586,524 proposes attaching on the PEI, lateral branches of poly(ethylene glycol) themselves functionalized by an addressable terminal group. Also, polyester amine)s prepared from polyether α-ω-diacrylate and from branched PEI (BPEI) have shown improved transfer efficiency with reduced toxicity (Kim et al., Macromolecular Bioscience 2007, 7, 611-619). This improvement technique was widely examined with many alternatives from BPEI or with LPEI of low molar mass (800 Da), notably by varying the nature of the diacrylate, for example with a short segment such as 1,3-butanediol diacrylate (Forrest et al., Bioconjugate Chemistry 2003, 14, 934-940). In the latter case, in order to obtain crosslinking or a highly branched product, PEI is dissolved in methylene chloride, a solvent in which the diacrylate used is also soluble. In a recent publication (Arote et al., Biomaterials 2007, 28, 735-744), the authors use linear poly(ethylenimine) with low molar mass for reacting with polycaprolactone diacrylate. In this work, it is sought to avoid the reaction of secondary amine functions of the PEI with the acrylate functions by benefiting from the fact that linear PEI has a primary amine function at each of its ends. For this purpose, the authors of this article conduct the reaction in methanol. The same applies in the work presented in another publication where PEI of low molar mass (423 Da) is reacted with poly(ethylene oxide)diacrylate with a mass from 250 to 700 Da (Park et al., Journal of Controlled Release 2005, 105, 367-380).

The use of imidazolyl functions for preparing polymeric transfer vectors was described in U.S. Pat. No. 7,163,695 for a polymer of the polypeptide type with at least 10 aminoacid residues. Indeed, at least 10% of these aminoacids are histidine residues but distributed in a non-random way. However, in the class of polyethylenimines, only the BPEIs were also modified by imidazolyl groups such as those found in histidine. The following reference gives details on the various attempts made up to now and describes how branched PEI (BPEI) may be modified by imidazolyl functions (Swami et al., International Journal of Pharmaceutics 2007, 335, 180-192). It should be noted that in this last reference, the authors only use branched PEI (BPEI) (25 kDa or 750 kDa), and their goal is to produce nanoparticles by means of subsequent crosslinking. This method was described in this reference by reaction of the primary amine groups with 4-imidazole-acetic acid hydrochloride activated with 1-ethyl-3-(3-dimethylaminopropyl)carbodiimide. It should be noted that if all these formulations proved to be more efficient than the starting BPEI (the 25 kDa PEI), they do not however attain the efficiency of linear PEIs although the latter are more toxic.

Therefore in the prior art, there exist many ways of modifying PEIs either by attempting to make them less toxic, or of improving their transfection efficiency. However, with none of these prior arts has it been possible to find a PEI which combines both of these advantages and in particular the efficiency of LPEIs with the low toxicity of BPEIs.

Surprisingly, the inventors have discovered that randomly attaching histidyl groups on linear polyethylenimine via a monoacrylate function substantially improves the transfection efficiency while reducing cell toxicity. With such a modification it is indeed possible to retain the globally linear structure of polyethylenimine, while reducing its toxicity and increasing the water solubility of the thereby modified polymer at physiological pHs. In other words, by means of such a modification, not only the efficiency of the LPEI is improved, which is already much better than that of BPEI, but toxicity is considerably reduced. Moreover this modification is performed by using an industrially simple method.

The present invention therefore relates to a random copolymer of linear polyethylenimine comprising the two monomeric units of the following formulae I and wherein $R_1$ represents a hydrogen atom or a $C_1$-$C_6$ alkyl group, $R_2$ represents a hydrogen atom, a $C_1$-$C_6$ alkyl, aryl or aralkyl group, in which the alkyl group is a $C_1$-$C_6$ alkyl, n is a number comprised between 1 and 99% of the total monomers and m is a number comprised between 1 and 99% of the total monomers.

Advantageously, this copolymer has an overall linear structure.

By the term of "$C_1$-$C_6$ alkyl radical", is meant in the sense of the present invention, any alkyl radical with 1-6 carbon atoms, either linear or branched, in particular, methyl, ethyl, n-propyl, iso-propyl, n-butyl, iso-butyl, sec-butyl, t-butyl, n-pentyl, n-hexyl groups. Advantageously, this is a linear group. In an advantageous way, this is a methyl group.

By the term of "aryl group", is meant in the sense of the present invention, one or more aromatic rings having 5-8 carbon atoms, which may be placed side by side. In particular, aryl groups may be monocyclic or bicyclic groups, preferably phenyl, naphthyl, biphenyl, tetrahydronapthyl, or indanyl groups. Advantageously this is a phenyl group.

By the term of "aralkyl group", is meant in the sense of the present invention, any aryl group as defined above, bound via an alkyl group as defined above. In particular, an aralkyl group is a benzyl group.

Advantageously, $R_1$ and $R_2$ either identical or different, represent a hydrogen atom or a $C_1$-$C_6$ alkyl group, in an advantageous way a hydrogen atom or a methyl group.

Thus, the random copolymer according to the invention may have the following formula VII:

wherein m, n, $R_1$ and $R_2$ are as defined earlier, or the following formula VIII:

wherein n, m, $R_1$ and $R_2$ are as defined earlier.

The advantage of the copolymer according to the invention lies in the fact that the histidine aminoacid is attached according to a random distribution on a linear polyethylenimine, via its primary amine function by means of a short spacer arm (—$CH_2$—$CH_2$—CO—) which transforms this primary amine function of histidine into a biocompatible amide function (—CO—NH—), identical with that corresponding to the attachment of histidine in the poly($\alpha$-amino-acid)s in proteins. Thus, the obtained copolymer is a random copolymer and not a block copolymer. Indeed, block copolymers seem to be particularly disadvantageous within the scope of the present invention since each block having different properties, there would be a risk of phase segregation and interaction with an anionic molecule and in particular the nucleic acid, different for each of the phases.

Further, the copolymer according to the invention globally keeps the linear structure of the LPEI and is therefore neither branched nor crosslinked.

Further, the copolymer according to the invention keeps the positive charge potential of the PEI since the monomer unit of formula II has a tertiary amine function always capable of being charged positively.

In an advantageous embodiment, m is less than 70% of the total monomers. Advantageously, m is comprised between 1 and 70% of the total monomers, more advantageously between 2 and 50% of the total monomers, still more advantageously between 4 and 40% of the total monomers, in an advantageous way between 5 and 35% of the total monomers, in a still more advantageous way between 10 and 30% of the total monomers.

In another advantageous embodiment, n is greater than 30% of the total monomers, advantageously n is comprised between 30 and 99% of the total monomers, more advantageously between 50 and 98% of the total monomers, still more advantageously between 60 and 96% of the total monomers, in an advantageous way between and 95% of the total monomers, in a still more advantageous way between 70 and 90% of the total monomers.

Advantageously m+n=100%.

Advantageously, the copolymer according to the invention may comprise an additional monomer unit of the following formula III:

wherein

$R_3$ represents a $C_1$-$C_6$ alkyl group, advantageously a methyl or ethyl group;

r is a number comprised between 0 and 95% of the total monomers, advantageously between 0 and 10% of the total monomers, in an advantageous way between 1 and 95% of the total monomers, in a still more advantageous way between 1 and 10% of the total monomers.

This monomer unit is also distributed randomly in the copolymer according to the invention.

Advantageously m+n+r=100%.

Thus, the random copolymer according to the invention may have the following formula IX:

IX wherein m, n, r, $R_1$, $R_2$ and $R_3$ are as defined earlier, or the following formula X:

X wherein m, n, r, $R_1$, $R_2$ and $R_3$ are as defined earlier, or the following formula XI:

XI wherein m, n, r, $R_1$, $R_2$ and $R_3$ are as defined earlier.

The copolymer according to the invention may also comprise monomer units including saccharide residues or poly (ethylene oxide) residues or peptide units, advantageously polylysine.

The saccharide residues are advantageously selected from residues of lactose, tetraglucose and mannose.

The saccharide residues and/or the poly(ethylene oxide) residues are grafted on the nitrogen atom of the PEI unit of formula I, advantageously via a C=O group.

In an advantageous way, the proportion of these residues is such that polyethylenimine is still globally of linear structure. Advantageously, each of these residues is present in the copolymer in a proportion of less than 70% of the total monomers, in an advantageous way, in a proportion of less than 50% of the total monomers and in a still more advantageous way in a proportion of less than 30% of the total monomers, still more advantageously in a proportion of less than 10% of the total monomers. In an advantageous way, each of these units is randomly positioned in the copolymer.

The present invention further relates to a method for preparing a copolymer according to the invention, characterized in that it comprises the step for putting a linear polyethylenimine solubilized in water at a pH comprised between 6.5 and 7.5 in contact with the compound of the following formula IV:

wherein $R_1$ and $R_2$ are as defined earlier, advantageously at the reflux temperature of water.

Therefore the method according to the invention may be applied in an aqueous phase which is a great simplification on the one hand and an advantage since a linear polyethylenimine) of low molar mass (for example the 22 kDa PEI) may thus be modified.

This method therefore consists in randomly modifying a linear polyethylenimine by reaction with a compound of formula IV.

With this reaction it is therefore possible to modify the secondary amine function of the PEI into a tertiary amine function. This addition reaction leads to partial and random transformation of ethylenimine units $CH_2$—$CH_2$—$NH$— into monomeric units substituted on the nitrogen atom with groups:

wherein § indicates the location where the molecule is grafted on the nitrogen and $R_1$ and $R_2$ are as defined earlier.

Further, as the compound of formula IV is a monoacrylate, by using it, it is possible to retain the globally linear structure of the macromolecular backbone of the thereby modified PEI and to avoid the formation of branched or crosslinked polymer.

With the modifications of the poly(ethylenimine) by the method according to the invention, it is possible to keep the positive charge potential of PEI since this modification transforms a secondary amine function into a tertiary amine function always capable of being positively charged.

The modification level of the PEI and therefore the value of m in the copolymer according to the invention depends on the duration of the step for putting the compound of formula IV into contact with the LPEI.

Advantageously, the duration of this step is at most 5 days, in an advantageous way, at most 4 days, in a more advantageous way at most 3 days, more advantageously at least 12 hours, even more advantageously at least 24 hours.

In an advantageous embodiment, the linear polyethylenimine before modification has a number average molecular mass comprised between 400 Da and 1,000,000 Da, advantageously between 4,000 and 40,000 Da, even more advantageously between 10,000 and 30,000 Da.

Advantageously, the LPEI which will react with the compound of formula IV is a random copolymer comprising the two monomeric units of formulae I and III as defined earlier.

Thus, this random copolymer may have the following formula XII:

wherein n, r, and $R_3$ are as defined earlier or the following formula XIII:

wherein n, r, and $R_3$ are as defined earlier.

This copolymer has an overall linear structure.

The LPEI which will react with the compound of formula IV may also comprise monomer units including saccharide residues or polyethylene oxide) residues or peptide units, advantageously polylysine.

The saccharide residues are advantageously selected from residues of lactose, tetraglucose and mannose.

The saccharide residues and/or the poly(ethylene oxide) residues are grafted on the nitrogen atom of the PEI unit of formula I, advantageously via a C=O group.

In an advantageous way, the proportion of these residues is such that polyethylenimine is always with an overall linear structure. Advantageously each of these residues is present in the copolymer in a proportion of less than 70%, in an advantageous way, in a proportion of less than 50% and in a still more advantageous way in a proportion of less than 30%, even more advantageously in a proportion of less than 10%.

In an advantageous way, each of these residues is randomly distributed in the LPEI.

The reaction between the LPEI and the compound of general formula IV does not modify the other possible monomer units present in the LPEI.

Advantageously, the LPEI which will react with the compound of formula IV, is obtained by acid hydrolysis of poly (2-$R_3$-2-oxazoline) with $R_3$ as defined earlier. The methods for preparing the LPEI are well-known to one skilled in the art, whether the LPEI contains or not monomer units of formula III and/or monomer units including saccharide residues or poly(ethylene oxide) residues and/or peptide units, advantageously polylysine. In particular, the monomer unit of formula III, as defined earlier, may for example originate from incomplete hydrolysis of the starting poly(2-$R_3$-2-oxazoline).

The compound of general formula IV may be obtained by reaction of the compound of the following general formula V wherein $R_2$ is as defined earlier, with a compound of the following general formula VI wherein $R_1$ is as defined earlier, advantageously in a basic medium, in an advantageous way, in the presence of soda, in particular in an aqueous phase. This process was in particular described in the article of Bentolila et al. (J. Med. Chem. 2000, 43, 2591-2600).

The present invention further relates to a pharmaceutical composition comprising a copolymer according to the present invention as a pharmaceutically acceptable vector, an active substance and optionally another pharmaceutically acceptable excipient.

Indeed, the copolymer according to the invention may be used for conveying an active substance towards the exact location where it should enter into action in an organ, a tissue or a cell.

By the term of "active substance", is meant in the sense of the present invention any pharmaceutical active ingredient (antalgics, antipyretics, aspirin, and derivatives, antibiotics, anti-inflammatory agents, antiulcerous agents, antihypertensive agents, neuroleptics, antidepressive agents, oligonucleotides, peptides, proteins for example); cosmetic (anti-UV, self-tanning agent for example), nutraceutical agent (vitamins for example); food industry agent; agrochemical or veterinary agent.

Advantageously, this active substance is negatively charged. In this case, this is therefore an anionic molecule.

These compositions may be formulated for administration to mammals, including humans. The dosage varies depending on the treatment and on the relevant affection. These compositions are made so as to be able to be administered via oral, sublingual, subcutaneous, intramuscular, intravenous, transdermal, local or rectal route. The suitable administration unit dosage forms comprise oral forms such as tablets, gelatin capsules, powders, granules and oral solutions or suspensions, sublingual and buccal administration dosage forms, subcutaneous, intramuscular, intravenous, intranasal or intraocular administration dosage forms, and rectal administration dosage forms.

Thus, the pharmaceutical composition according to the present invention may comprise another pharmaceutically acceptable excipient such as gelatin, starch, lactose, magnesium stearate, talc, gum arabic or the like, a sweetener, an antiseptic as well as a gustatory agent, a suitable coloring agent, dispersion agents or wetting agents, suspension agents or a diluent. The tablets of the composition according to the invention may be coated with saccharose or other suitable materials or further they may be treated in such a way that they have prolonged or delayed activity and continuously release a predetermined amount of active ingredient and of copolymer according to the invention.

For rectal administration, suppositories are resorted to, which are prepared with binders melting at the rectal temperature, for example cocoa butter or polyethylene glycols.

For parenteral, intranasal or intraocular administration, aqueous suspensions, isotonic saline solutions or sterile and injectable solutions are used which contain pharmacologically compatible dispersion agents and/or wetting agents.

The present invention further relates to the use of a copolymer according to the present invention as a pharmaceutically acceptable vector of an active substance in a pharmaceutical composition.

The present invention further relates to a complex comprising
a) the copolymer according to the present invention
b) at least one anionic molecule.

In such a complex, the bond between the compound a) and the compound b) is of electrostatic nature. Indeed, within the scope of complexes according to the invention, the copolymer according to the invention is found in cationic form.

Advantageously, the anionic molecule is a nucleic acid.

In the complex according to the present invention, the nucleic acid may also be both a deoxyribonucleic acid (DNA) and a ribonucleic acid (RNA) or hybrid DNA/RNA sequences. These may be sequences of natural or artificial origin, and notably of genomic DNA, complementary DNA (cDNA), messenger RNA (mRNA), transfer RNA (tRNA), ribosomal RNA (rRNA), or synthetic or semi-synthetic sequences. Further, the nucleic acid may have very variable size ranging from oligonucleotides to chromosomes. These nucleic acids may be of human, animal, plant, bacterial, viral origin, etc. They may be obtained by any technique known to one skilled in the art and notably by bank screening, by chemical synthesis or further by mixed methods including chemical or enzymatic modification of sequences obtained by bank screening. They may also be obtained by chemical modification at their sugar portions, at their nucleobase portions or at their internucleotide backbone. Among advantageous modifications in the sugar portions, mention may notably be made of the modifications involved in the 2' position of the ribose, such as 2'-dioxy, 2'-fluoro, 2'-amino, 2'-thio, or 2'-O-alkyl, in particular 2'-O-methyl modifications, instead of the normal 2'-OH group on ribonucleotides, or further the presence of a methylene bridge between the 2' and 4' positions of the ribose (LNA). As regards the nucleobases, it is possible to use modified bases, such as notably 5-bromo-uridine, 5-iodo-uridine, $N^3$-methyl-uridine, a 2,6-diaminopurine (DAP), 5-methyl-2'-dioxycytidine, 5-(1-propynyl)-2'-deoxy-uridine (pdU), 5-(1-propynyl)-2'-deoxy-cytidine (pdC), or conjugate bases with cholesterol. Finally, advantageous modifications of the internucleotide backbone comprise the replacement of phosphodiester groups of this backbone with phosphorothioate, methylphosphonate, phosphorodiamidate groups, or the use of a backbone consisting of N-(2-amino-ethyl)-glycine units bound by peptide bonds (PNA, Peptide Nucleic Acid). The different modifications (base, sugar, backbone) may of course be combined in order to obtain modified nucleic acids of the morpholine type (bases fixed on a morpholine cycle and bound by phosphorodiamidate groups) or of the PNA type (bases fixed on N-(2-aminoethyl)-glycine units bound by peptide bonds).

Moreover they may be incorporated in vectors such as plasmid vectors.

Advantageously, the nucleic acid is selected from the group formed by RNA, complementary DNA (cDNA), genomic DNA, plasmid DNA, antisense DNA, messenger RNA, antisense RNA, interfering RNA, ribozymes, transfer RNA, ribosomal RNA, or DNA coding for these RNA types.

More particularly as regards deoxyribonucleic acids, they may be with a single or double strand. These nucleic acids may comprise a sequence of genes selected from a) marker genes, b) genes with a therapeutic purpose and c) genes with a vaccinal purpose, and elements allowing its expression.

In the sense of the invention, by "gene with a therapeutic purpose" is notably meant any gene coding for a protein product having a therapeutic effect. The thereby coded protein product may be a protein, a peptide, etc. This protein product may be homologous towards the target cell (i.e. a product which is normally expressed in the target cell when the latter does not have any pathology). In this case, by expression of a protein, it is for example possible to find a remedy to insufficient expression in the cell or to expression of an inactive or weakly active protein because of a modification, or further to overexpression of said protein. The therapeutic gene may also code for a mutant of a cell protein, having increased stability, modified activity, etc. The protein product may also be heterologous towards the target cell. In this case, an expressed protein may for example complete or provide an activity which is lacking in the cell, allowing it to fight against a pathology or stimulate an immune response. The therapeutic gene may also code for a protein secreted in the organism.

The therapeutic gene may also be an anti-sense gene or sequence, the expression of which in the target cell allows control of the expression of genes or transcription of cell RNAs. Such sequences may for example be transcribed in the target cell, into complementary RNA of cell mRNAs and thereby block their translation into a protein. These may also be synthetic, possibly modified oligonucleotides. The anti-senses also comprise sequences coding for ribozymes, which are capable of selectively destroying the target RNAs. The therapeutic gene may also be a gene coding for siRNA or shRNA.

Advantageously, the genes with a therapeutic purpose are selected from the genes coding for:
dystrophin and minodystrophin (myopathies);
cystic fibrosis transmembrane conductance regulator protein (CFTR) associated with cystic fibrosis;
alpha1-antitrypsin;
erythropoietin (FPO);
cytokines such as interleukins and tumor necrosis factor TNF;
growth factors such as TGF-beta and PDGF;
lysosomal enzymes such as beta-glucosidase;
adenosine deaminase (ADA);
sense and anti-sense RNAs;
interfering RNAs;
ribozymes;
receptors of low density lipoproteins, lacking in the case of hypercholesterolemia;
coagulation factors such as the factors VII, VIII and IX;
phenylalanine-hydroxidase;
tyrosine hydroxylase;
thymidine kinase of the Herpes simplex virus;
proteins of the major histocompatibility complex, advantageously HLA-B7s;
cytosine deaminase.

As indicated above, the nucleic acid may also includes one or more genes with a vaccinal purpose capable of generating an immune response in humans or animals. In this particular embodiment, the invention therefore allows the production of vaccines or immunotherapeutic treatments applied to humans or animals, notably against microorganisms, parasites, bacteria, viruses or cancers. These may notably be antigenic peptides specific to the Epstein Barr virus, to the HIV virus, to the B hepatitis virus, to the pseudo-rabies virus, or further specific to tumors.

Thus, advantageously, the genes with a vaccinal purpose are selected from the genes coding for:
viral antigens, advantageously the nucleoprotein of the influenza virus or the NEF or GAG protein of the HIV virus;
antigens associated with tumors, advantageously the MART1 antigen of melanoma cancers, mucins or the PSA antigen of prostate cancers;
bacterial antigens;
parasite antigens.

In another advantageous embodiment, the marker gene is selected from the genes of:
luciferase of fireflies;
green protein of *Aequora Victoria* jellyfishes;
beta-galactosidase of *E. coli*;
chloramphenicol acetyl transferase;
resistance to an antibiotic, advantageously resistance to neomycin or hygromycin.

In order to obtain an optimum effect of the complexes of the invention, the respective proportions of the polymer and of the nucleic acid are preferably determined so that the mass ratio (µg/µg) between the polymer and the nucleic acid is comprised between 1/3 and 1/4.

This ratio may of course be adapted by skilled in the art depending on the copolymer used, on the presence of an adjuvant (see hereafter), on the nucleic acid, on the target cell and on the mode of administration used.

The complexes according to the invention may be prepared by mixing a solution of the relevant nucleic acid and a solution of the copolymer according to the invention. Advantageously, these solutions are prepared from physiological saline solution or from a buffer such as hepes buffer or a cytocompatible medium.

The present invention further relates to a pharmaceutical composition comprising a complex according to the invention and optionally a pharmaceutically acceptable excipient.

The pharmaceutical composition according to the invention may be used as such or in combination with other compounds. Thus, in a particular embodiment, the composition according to the present invention further comprises an adjuvant capable of being combined with the copolymer/nucleic acid complex according to the invention and of improving the transfecting power. Indeed, the transfecting power of the compositions of the invention may further be improved in the presence of certain adjuvants (lipids, proteins, lipopolyamines, synthetic polymers for example), capable of being combined with the copolymer/nucleic acid complex according to the invention.

Advantageously, the adjuvants used in the compositions according to the invention are cationic lipids (including one or more cationic charges in their polar portion) or neutral lipids.

As regards cationic lipids, these may more particularly be lipopolyamine. Other particularly advantageous adjuvants for making the compositions of the invention are represented by neutral lipids. The use of neutral lipids is particularly advantageous when the charge ratio R (amines/phosphates) is low. In a particularly advantageous way, natural or synthetic, zwitterionic lipids or those without any ionic charge under physiological conditions are used. These different lipids may be obtained either by synthesis, or by extraction from organs (example: the brain) or from eggs, by standard techniques well-known to one skilled in the art.

In a particularly advantageous embodiment, the compositions of the present invention comprise a targeting element allowing orientation of the transfer of nucleic acid. This targeting element may be an extracellular targeting element, allowing transfer of the nucleic acid to be directed towards certain cell types of certain desired tissues (tumor cells, hepatic cells, hematopoietic cells, etc.). This may also be an intracellular targeting element, allowing the transfer of the nucleic acid to be directed towards certain preferential cell compartments (mitochondria, nucleus, etc.).

Among the targeting elements which may be used within the scope of the invention, mention may be made of sugars, peptides, oligonucleotides, lipids or proteins. Advantageously, these are sugars, peptides or proteins such as antibodies or antibody fragments, ligands of cell receptors or fragments of the latter, receptors or receptor fragments, etc. In particular, these may be ligands of growth factor receptors, of cytokine receptors, of cell lectin receptors or of adhesion protein receptors. Mention may also be made of the receptor of transferrin, HDLs and LDLs. The targeting element may also be a sugar allowing targeting of asialoglycoprotein receptors, or further an antibody Fab fragment for targeting the receptor of the fragment Fc of immunoglobulins.

The compositions according to the invention may be formulated with view to administrations via a topical, cutaneous, oral, rectal, vaginal, parenteral, intranasal, intravenous, intramuscular, subcutaneous, intraocular, transdermal route, etc. Preferably, the pharmaceutical compositions of the invention contain a pharmaceutically acceptable carrier for an injectable formulation, notably for direct injection at the desired organ, or for administration via a topical route (on the skin and/or a mucosa). These may in particular be sterile, isotonic solutions, or dry compositions, notably freeze-dried compositions, which by addition of sterilized water or of physiological saline depending on the case, allow formation of injectable solutes. The nucleic acid doses used for the injection as well as the number of administrations may be adapted depending on different parameters, and notably depending on the mode of administration used, on the relevant pathology, on the gene to be expressed, or further on the sought duration of the treatment.

As indicated hereinbefore, the complexes and compositions according to the invention may be used for transferring nucleic acid into cells in vivo, in vitro or ex vivo. In particular, the copolymers according to the invention may be used for transferring in a very efficient way nucleic acids into many cell types, and in particular in certain cell types which are usually difficult to transfect.

Thus, the present invention relates to a method for transferring in vitro or ex vivo a nucleic acid into cells, said method comprising the putting of said cells into contact with at least one complex according to the present invention or a pharmaceutical composition according to the invention.

The cells may be of prokaryotic or eukaryotic origin, in particular animal, plant or human origin.

Advantageously, the cells are mammal cells, advantageously selected from:
  hematopoietic stem cells;
  cells of the immune system, such as dendritic cells, macrophages and lymphocytes;
  liver cells;
  cells of skeletal muscles;
  skin cells, such as fibroblasts, keratinocytes, dendritic cells and melanocytes;
  cells of blood vessels and microvessels, such as endothelial cells and smooth muscle cells;
  epithelial cells of airways;
  cells of the central nervous system;
  cancer cells;
  cells of the connective tissue, such as tenocytes.

According to an advantageous embodiment of the invention, the in vitro or ex vivo transfection method is characterized in that a complex or a pharmaceutical composition according to the invention is put into presence in a medium containing cells to be transfected, under conditions such that there is:
  passage of the complex from the medium into the cytoplasm of the cells,
  desalting of the nucleic acid involved in the aforesaid complex in the cytosol and/or in the nucleus of the cells,
  transcription and expression of the nucleic acid in the transfected cells,
  expression of the protein corresponding to the transfected gene.

The present invention further relates to the use of a copolymer according to the invention for preparing a pharmaceutical composition intended for intracellular delivery of anionic molecules, advantageously nucleic acid molecules.

It further relates to a complex according to the invention for its use as a drug intended for intracellular delivery of nucleic acid, advantageously intended for treating tumors, more advantageously uterine leiomyoma or a malignant tumor such as carcinoma of the ovaries, of the breast or of the endometrium, for preparing a vaccine or for treatment or prevention of congenital or acquired metabolic deficiency or of diseases associated with deficient genetic expression, more advantageously for the treatment of diseases related to the disorders of a single gene such as severe combined immunodeficiency syndromes, cystic fibrosis, hemophilia, drepanocytosis, beta-thalassemia and muscular dystrophy.

The invention will be better understood upon reading the examples and examining the figures which follow.

FIG. 1 illustrates the migration of plasmid DNA in electrophoresis in an agarose gel in the presence of ethydium bromide. The DNA band corresponding to the migration of 1 µg of DNA in the absence of polymer. For the copolymer according to the invention with m=25% and $R_1$ and $R_2$=H (His-LPEI(25%)), a non-modified LPEI (LPEI) and the copolymer according to the invention with m=66% and $R_1$ and $R_2$=H (His-LPEI(66%)), the bands 1, 2, 3 and correspond to the migration of 1 µg of DNA in the presence of 1, 2, 3 and 4 µg of polymer or copolymer. The DNA is revealed under UV light.

The following examples illustrate the invention without limiting the scope thereof.

The copolymers of polyethylenimines according to the invention are tested for their properties of transfection of various cell lines, for example by means of plasmid coding for luciferase.

EXAMPLE 1

Copolymer According to the Invention: $R_1$=$R_2$=H, m=25% and Complex with DNA of a Reporter Gene Coding for Luciferase Preparation of the Copolymer According to the Invention:
An LPEI copolymer according to the invention with $R_1$=$R_2$=H and m=25% is prepared in the following way:
One starts by preparing linear polyethylenimine (LPEI) from poly(2-methyl-2-oxazoline) by acid hydrolysis:
10 g of poly(2-methyl-2-oxazoline) with a molar mass of 50,000 Da (Aldrich) are dissolved in 115 mL of distilled water, to which are added 75 mL of 37% hydrochloric acid (Aldrich). This is heated with reflux for 24 hours. After cooling, soda tablets are added in order to bring the reaction medium to pH=14. LPEI precipitates. The precipitate is washed with distilled water until a neutral wash is obtained. The precipitate is then washed with acetone and the thereby obtained LPEI is dried in vacuo. The yield is 98% and the product is checked by nuclear magnetic resonance.

The synthesis of the N-2-(3(3H-imidazol-4-yl)propanoic acid)acrylamide (product of formula IV, $R_1$ and $R_2$=H) is carried out in the following way: 3.1 g of histidine (Aldrich) are dissolved in 100 mL of distilled water containing 3 g of soda. 1.8 g of acryloyl chloride (Aldrich) are added dropwise with stirring at room temperature. The sought product is recovered by concentrating the reaction medium, precipitation in acetone and filtration. The product is then dried in vacuo.

The modification of the LPEI is carried out in the following way: 3.7 g of LPEI prepared as above, 3 g of N-2-(3(3H-imidazol-4-yl)propanoic acid)acrylamide are dissolved in 40 mL of distilled water. This is heated with reflux for 2 days. After cooling to an ordinary temperature, this is dry evaporated and taken up with 20 mL of methanol. The portion which is not soluble in methanol is the sought product. This is finished with drying in vacuo. With this operating procedure it is possible to obtain the copolymer according to the invention with 25% modification of the ethylenimine units (m=25%).

Figure 1:
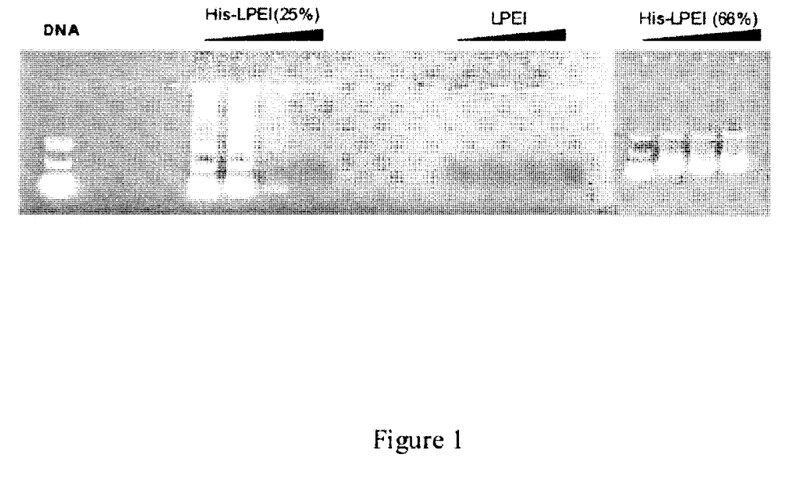

The transfection efficiency of the copolymer according to the invention, as obtained above, was tested in vitro and measured by means of a reporter gene coding for luciferase under the control of the CMV promoter. It was compared with the transfection efficiency of a non-modified LPEI.
Preparation of Complexes According to the Invention and of the Non-Modified LPEI/DNA Complex:
In order to determine optimum formation of the DNA/copolymer complexes according to the invention and of DNA/non-modified LPEI complexes, different mixtures were prepared according to the following procedure and analyzed by electrophoresis on 0.6% agarose gel:

30 µL of a polymer solution in an amount of 1 mg/mL are diluted in 60 µL of 10 mM Hepes buffer, pH 7.4. This polymer solution is then transferred into 140 µL of 10 mM Hepes buffer, pH 7.4 containing 7.5 µg of plasmid coding for luciferase. The mixture is intensively stirred for 4 s and then left at rest at 20° C. for 30 min. 20 µL of the mixture are analyzed by electrophoresis on 0.6% agarose gel containing ethydium bromide allowing DNA to be revealed by UV irradiation. The mixtures allowing total non-migration of DNA are considered as being those which contain DNA totally condensed with a polymer (FIG. 1). These complexes are those which will be used for transfecting cells, i.e. for the DNA/non-modified LPEI complexes in a mass ratio 1/2 (µg:µg), or 1/3 (µg:µg) and 1/4 (µg:µg) for DNA/copolymer complexes according to the invention. As indicated by the agarose gel, when LPEI is substituted in an amount of 66% with histidine (copolymer according to the invention with $R_1$=$R_2$=H and m=66%), the interactions of the polymer with the DNA are weak and there is an absence of strong DNA condensation. The size and the global charge (zeta potential) of the complexes are measured by means of the Zetasizer 3000 (Malvern Instruments). The DNA/non-modified LPEI complexes have a size of 78 nm and a zeta potential of 13 mV, the size of the DNA/LPEI complexes according to the invention with $R_1$=$R_2$=H and m=25% is 250 nm and the zeta potential is 8 mV.
In Vitro Transfection Tests:

HeLa cells were sown in a 24-well plate with an initial density of $2 \times 10^5$ cells per well. They were subject to incubation for 18-20 hours in order to attain 80% confluence. The solutions of DNA/polymer complexes described above are adjusted to 1.5 mL with cell culture medium containing 10% fetal calf serum. The medium of the cells is then replaced with 0.5 mL of the mixture containing the LPEI/DNA complex coding for luciferase (2.5 µg/well) or the copolymer complex according to the invention (with $R_1$=$R_2$=H and m=25%))/DNA complex coding for luciferase (2.5 µg/well). 4 hours incubation is then carried out at 37° C. in an oven with 95% air and 5% $CO_2$. The medium is then replaced with a medium containing 10% of fetal calf serum and maintained for 48 hours in an incubator at 37° C. The luciferase activity tests are carried out according to the procedure described in Pichon et al. (J. Gene Med. 2002, 4, 548-559), and the emitted light intensity was then normalized to the amount of produced protein after a BCA assay according to the operating method described in the same reference.

Figure 2:
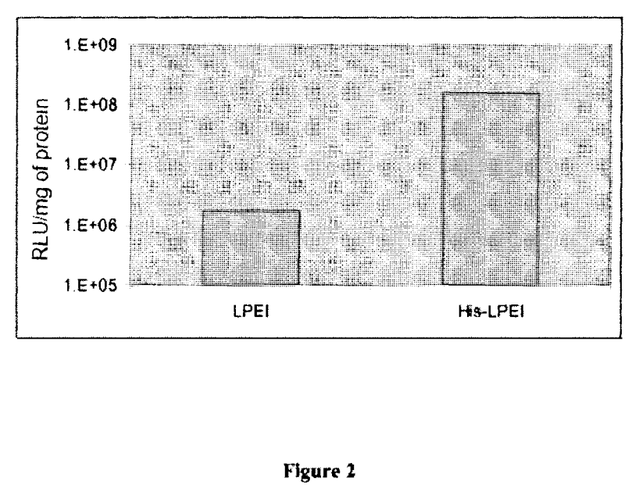
FIG. 2 illustrates the measurement of luciferase activity (RLU) 48 hrs after transfection of HeLa cells with 2.5 µg of plasmid coding for the luciferase complexed with the non-modified LPEI (LPEI) or with the copolymer according to the invention with m=25% and $R_1$ and $R_2$=H (His-LPEI).

The results are the following:
The non-modified LPEI gives a luciferase activity of $1.7 \cdot 10^6$ RLU/mg of protein while the copolymer according to the invention with $R_1$=$R_2$=H and m=25% gives a luciferase activity of $1.5 \cdot 10^8$ RLU/mg of protein (FIG. 2).

Figure 3:
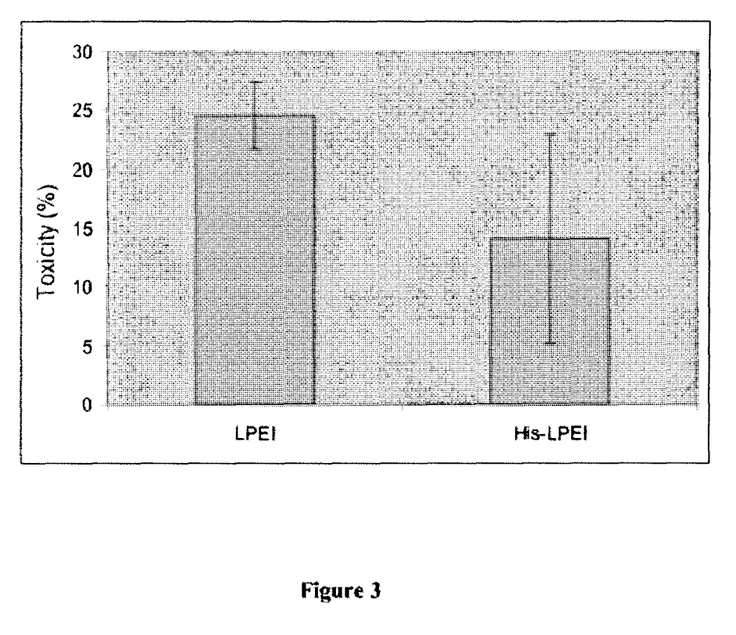
FIG. 3 illustrates the measurement of toxicity induced by transfection of HeLa cells with 2.5 µg of plasmid coding for luciferase complexed with non-modified LPEI (LPEI) or with the copolymer according to the invention with m=25% and $R_1$ and $R_2$=H (His-LPEI). Cell viability is measured 48 hrs after transfection by a colorimetric assay using MTT.

Thus, not only the transfection efficiency is increased, but toxicity is considerably reduced: by using the MTT assay, the measured toxicity is 26% for non-modified LPEI, it is only 14% for the copolymer according to the invention with $R_1$=$R_2$=H and m=25% (FIG. 3).

EXAMPLE 2

Figure 4:
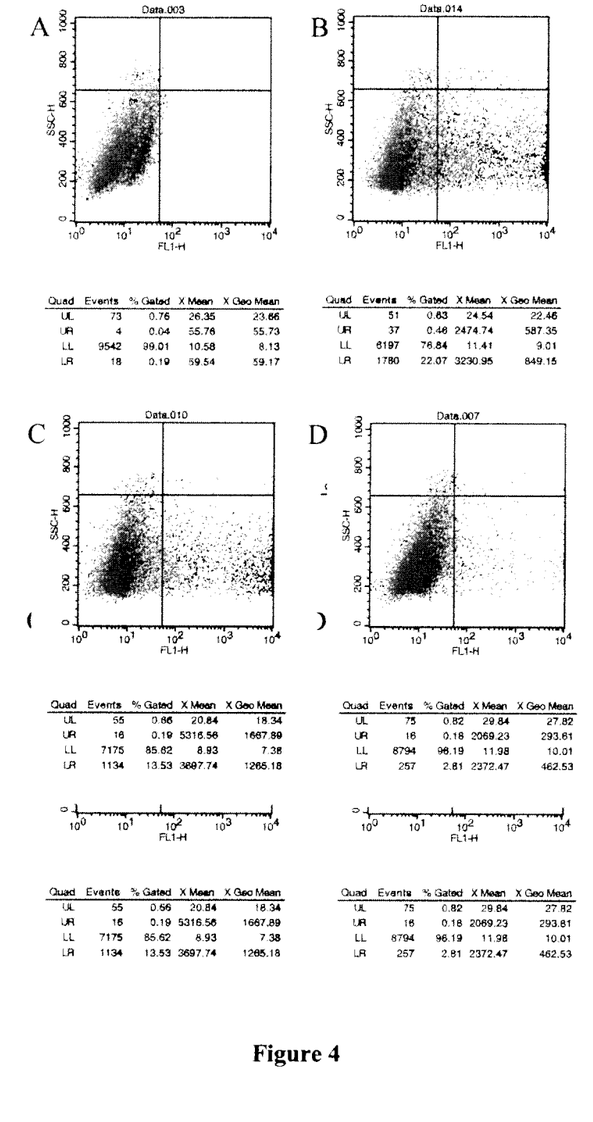
FIG. 4 represents the evaluation of the number of transfected HeLa cells with 2.5 µg of plasmid coding for the green jellyfish protein (pCMV-EGFP) complexed with non-modified LPEI (D) or with the copolymer according to the invention with $R_1$ and $R_2$=H and m=25% (B) or m=4% (C), as compared with non-transfected cells (A). The number of cells expressing EGFP is determined after measuring fluorescence of the cells (FL1-H) by flow cytometry 48 hrs after transfection.

Copolymer According to the Invention: $R_1$=$R_2$=H, m=25% and Complex with the DNA of a Plasmid Coding for Green Fluorescent Jellyfish Protein The same transfection tests are carried out as in Example 1 from the copolymer obtained in Example 1 but a plasmid coding for the green fluorescent jellyfish protein (EGFP) is used here. By measuring fluorescence of the cells in flow cytometry it is possible to reach the number of transfected cells as well as the intensity of the expression of the gene in the cells and the viability of the cells in the presence of propidium iodide. The results shown in FIG. 4 indicate that 22% and 13% of HeLa cells respectively transfected with the copolymer according to the invention ($R_1=R_2=H$ and m=25% and m=4%) express the transgene. The number of transfected cells by non-modified LPEI is small (about 3%).

EXAMPLE 3

Copolymer According to the Invention: $R_1=R_2=H$, m=4% and Complex with the DNA of a Reporter Gene Coding for Luciferase The same copolymer syntheses are conducted as in Example 1 above, with the only difference that chemical modification of the monomer units of LPEI is carried out by means of 3-amidopropionato-1-yl-(3-(3H-imidazol-4-yl) propanoic acid groups at a rate of only 4%. This rate is obtained by only heating LPEI with reflux in contact with the modifying agent for one day. Under the same conditions as in Example 1, the efficiency of 4% modified LPEI (copolymer according to the invention with $R_1=R_2=H$ and m=4%) is of about $1.10^7$ RLU/mg of protein (FIG. 5), to be compared with an efficiency of $1.7\ 10^6$ RLU/mg of protein for non-modified LPEI (FIG. 1).

EXAMPLE 4

Figure 5:
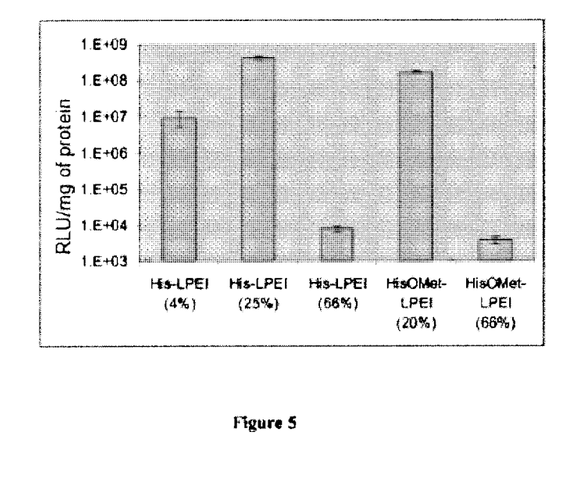
FIG. 5 represents the measurement of luciferase activity (RLU) 48 hrs after transfection of HeLa cells with 2.5 µg of plasmid coding for the luciferase complexed with the copolymer according to the invention with $R_1$ and $R_2$=H and m=4%, 25% or 66% or with the copolymer according to the invention with $R_1$=H and $R_2$=methyl and m=20% or 66%.

Copolymer According to the Invention: $R_1=R_2=H$, m=66% and Complex with the DNA of a Reporter Gene Coding for Luciferase The same copolymer syntheses are conducted as in Example 1 above, with the only difference that chemical modification of the monomeric units of LPEI is carried out with 3-amidopropionato-1-yl-(3-(3H-imidazol-4-yl)pro- panoic acid groups at a rate of 66%. This rate is obtained by heating LPEI with reflux in contact with the modifying agent for a period of four days. Under the same conditions as in Example 1, the efficiency of the 66% modified LPEI (copolymer according to the invention with $R_1=R_2=H$ and m=66%) is about $1.10^4$ RLU/mg of protein (FIG. 5).

EXAMPLE 5

Copolymer According to the Invention: $R_1=H$, $R_2=$Methyl and m=20% or m=66% and Complex with the DNA of a Reporter Gene Coding for Luciferase The same copolymer syntheses are conducted as in Example 1 above, with the only difference that chemical modification of the monomeric units of LPEI is carried out with 3-amidopropionato-1-yl-(3-(3H-imidazol-4-yl)pro- panoate methyl ester groups at a rate of 20%. Synthesis of N-2-(3(3H-imidazol-4-yl)propanoate methyl ester)acryla- mide (compound of formula IV with $R_1=H$ and $R_2=-CH_3$) is carried out in the following way: this modifying agent is obtained under the same conditions as in Example 1, by replacing histidine by its methyl ester: N-2-(3(3H-imidazol- 4-yl)propanoate methyl ester)acrylamide. The rate of 20% is obtained by heating LPEI with reflux in contact with the modifying agent for a period of 2 days. Under the same conditions as in Example 1, the efficiency of 20% modified LPEI (copolymer according to the invention with $R_1=H$, $R_2=$methyl and m=20%) is about $1.6.10^8$ RLU/mg of protein, which is comparable with the one obtained with histidine in its acid form (Example 1, FIG. 2 and FIG. 5: His-LPEI at 25% and HisOMet-LPEI at 20%). On the other hand, the transfec- tion obtained with 66% modified LPEI is very low (copoly- mer according to the invention, $R_1=R_2=$methyl and m=66%), around about $4.10^3$ RLU/mg of protein (FIG. 5: HisOMet-LPEI at 66%). This result is consistent with the fact that this LPEI which is too highly substituted with histidine, does not strongly condense the DNA (FIG. 1).

Thus, through these examples, the inventors have shown that linear polyethylenimines modified according to the invention not only have a higher transfection efficiency than that of corresponding non-modified polyethylenimines, but they also have less toxicity. The advantage of this modifica- tion does not only lie in the improvement in transfection efficiency, but also in the fact of keeping a linear structure for the macromolecular backbone and of increasing solubility in water of the thereby modified polymer at physiological pHs.

According to the modification rate, the efficiency and tox- icity vary, and this depending on the nature of the transfected cells.

The invention claimed is:

1. A random copolymer of linear polyethylenimine com- prising the two monomeric units of the following formulae I and II:

wherein
$R_1$ represents a hydrogen atom or a $C_1$-$C_6$ alkyl group,
$R_2$ represents a hydrogen atom, a $C_1$-$C_6$ alkyl, aryl or aralkyl group, in which the alkyl group is a $C_1$-$C_6$ alkyl,
n is a number comprised between 1 and 99% of the total monomers and
m is a number comprised between 1 and 99% of the total monomers.

2. The copolymer according to claim 1, wherein m is com- prised between 1 and 70% of the total monomers.

3. The copolymer according to claim 1, wherein it com- prises an additional monomer unit of formula III:

wherein

R$_3$ represents a C$_1$-C$_6$ alkyl group;

r is a number comprised between 1 and 95% of the total monomers.

4. A method for preparing a copolymer according to claim 1, wherein it comprises a step for putting a linear polyethylenimine solubilized in water at a pH comprised between 6.5 and 7.5 in contact with the compound of the following formula IV:

IV wherein R$_1$ represents a hydrogen atom or a C$_1$-C$_6$ alkyl group, and R$_2$ represents a hydrogen atom, a C$_1$-C$_6$ alkyl, aryl or aralkyl group, in which the alkyl group is a C$_1$-C$_6$ alkyl.

5. The method according to claim 4, wherein the linear polyethylenimine has a number average molar mass comprised between 400 Da and 1,000,000 Da.

6. The method according to claim 4, wherein the compound of general formula IV is obtained by reacting the compound of the following general formula V

V wherein R$_2$ represents a hydrogen atom, a C$_1$-C$_6$ alkyl, aryl or aralkyl group, in which the alkyl group is a C$_1$-C$_6$ alkyl, with a compound of the following general formula VI

VI wherein R$_1$ represents a hydrogen atom or a C$_1$-C$_6$ alkyl group.

7. A pharmaceutical composition comprising a copolymer according to claim 1 as a pharmaceutically acceptable vector and an active substance.

8. A pharmaceutically acceptable vector of an active substance in a pharmaceutical composition which comprises the copolymer according to claim 1.

9. A complex comprising
a) the copolymer according to claim 1, and
b) at least one anionic molecule.

10. The complex according to claim 9, wherein the anionic molecule is a nucleic acid selected from the group formed by RNA, cDNA, genomic DNA, plasmid DNA, antisense DNA, messenger RNA, antisense RNA, interfering RNA, ribozymes, transfer RNA, ribosomal RNA, and DNA coding for these RNA types.

11. The complex according to claim 9, wherein the anionic molecule is a nucleic acid which comprises a sequence of genes selected from a) marker genes, b) genes with therapeutic purpose and c) genes with vaccinal purpose, and elements allowing its expression.

12. The complex according to claim 11, wherein the marker gene is selected from the genes of:
luciferase of fireflies;
green protein of *Aequora Victoria* jellyfishes;
beta-galactosidase of *E. coli;*
chloramphenicol acetyl transferase; and
resistance to an antibiotic.

13. The complex according to claim 11, wherein the genes with vaccinal purpose are selected from the genes coding for:
viral antigens;
antigens associated with tumors;
bacterial antigens; and
parasite antigens.

14. The complex according to claim 11, wherein the genes with a therapeutic purpose are selected from the genes coding for:
dystrophin and minidystrophin;
cystic fibrosis transmembrane conductance regulator protein (CFTR) associated with cystic fibrosis;
alpha1-antitrypsin;
erythropoietin (EPO);
cytokines;
growth factors;
lysosomal enzymes;
adenosine deaminase;
sense and anti-sense RNAs;
interfering RNAs;
ribozymes;
receptors of low density lipoproteins, lacking in the case of hypercholesterolemia;
coagulation factors such as the factors VII, VIII and IX;
phenylalanine-hydroxidase;
tyrosine hydroxylase;
thymidine kinase of the Herpes simplex virus;
proteins of the major histocompatibility complex; and
cytosine deaminase.

15. A pharmaceutical composition comprising a complex according to claim 9.

16. The random copolymer according to claim 1 wherein m+n=100%.

17. The random copolymer according to claim 3 wherein m+n+r=100%.

18. The complex according to claim 9 wherein the anionic molecule is a nucleic acid.

* * * * *